(12) United States Patent
Seiler

(10) Patent No.: US 7,204,796 B1
(45) Date of Patent: Apr. 17, 2007

(54) DEVICE FOR DETERMINING THE POSITION OF BODY PARTS AND USE OF THE SAME

(75) Inventor: Paul G. Seiler, Villigen (CH)

(73) Assignee: Northern Digital Inc., Waterloo, Ontario (CA)

( * ) Notice: Subject to any disclaimer, the term of this patent is extended or adjusted under 35 U.S.C. 154(b) by 0 days.

(21) Appl. No.: 10/182,891

(22) PCT Filed: Feb. 2, 2000

(86) PCT No.: PCT/CH00/00055

§ 371 (c)(1),
(2), (4) Date: Dec. 23, 2002

(87) PCT Pub. No.: WO00/22904

PCT Pub. Date: Apr. 27, 2000

(51) Int. Cl.
*A61N 5/00* (2006.01)
(52) U.S. Cl. .......................................................... 600/3
(58) Field of Classification Search ................ 600/1–8, 600/424, 426, 427; 128/899
See application file for complete search history.

(56) References Cited

U.S. PATENT DOCUMENTS

| 5,335,669 A | 8/1994 | Tihon et al. |
| 5,785,051 A | 7/1998 | Lipscher et al. |
| 5,899,860 A | 5/1999 | Pfeiffer et al. |
| 5,938,605 A | 8/1999 | Hasing et al. |
| 6,251,059 B1 * | 6/2001 | Apple et al. .................... 600/3 |
| 6,402,689 B1 * | 6/2002 | Scarantino et al. .......... 600/300 |

FOREIGN PATENT DOCUMENTS

| EP | 0 829 229 A1 | 3/1998 |
| NL | 1004381 | 5/1998 |
| WO | WO 97/36192 | 10/1997 |

OTHER PUBLICATIONS

Chinese Patent Abstract of Chinese Patent No. CN1202809, Publication Date: Dec. 23, 1998, Applicant: Photoelectron Corp.

* cited by examiner

*Primary Examiner*—John P. Lacyk
(74) *Attorney, Agent, or Firm*—Fish & Richardson P.C.

(57) ABSTRACT

The invention relates to a device consisting of a catheter (K) for introducing into the human or animal body and to the use of said device. The inventive device is characterized in that at least a part of the catheter is elastic. At least one sensor unit (PS) for determining the current position is provided at least in the elastic part of the catheter (KK), preferably on its inner surface. Outside the body, a receiver unit is provided to which the signals measured by the sensor unit (PS) are transmitted.

17 Claims, 1 Drawing Sheet

DEVICE FOR DETERMINING THE POSITION OF BODY PARTS AND USE OF THE SAME

Figure 1:
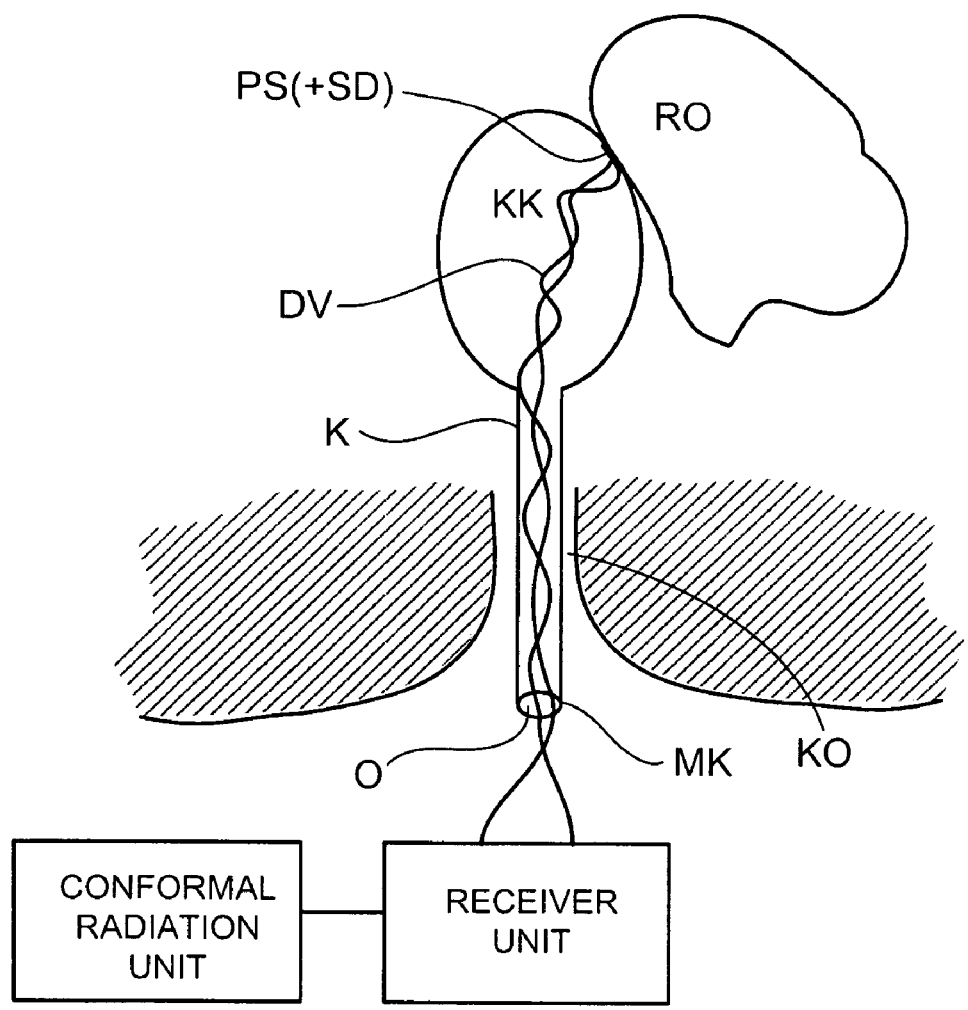

The present invention relates to a device as defined in the preamble to Claim 1, and the use of the device.

Modern radiation therapy for the treatment of tumors is targeted at their destruction through the application of a high dose of radiation that is lethal to the tumor. This is always difficult if there are organs in the immediate vicinity of the tumor that can tolerate only small amounts of radiation (so-called risk organs). In the abdominal and chest cavities, there is the additional difficulty arising from the fact that, in these regions, tumors and the adjacent risk organs move within the patient's body. The geometrical target region of radiation is therefore not fixed in place; consequently, adjacent healthy organs or parts thereof frequently receive an unnecessarily high dose of radiation in these cases. The causes of the aforementioned movements are lung movements during respiration, the heartbeat and intestinal activity. The position of tumors and organs can also change due to the changing health status of the patient, or because of his various positions.

Today, modern radiation equipment can be used in the body of a patient to intensively irradiate a three-dimensional region (high-dose volume) in such a way that the shape of this region precisely mimics the shape of the tumor (conformal radiation therapy). It is particularly important in this connection that the high-dose volume exclude adjacent risk organs (conformal avoidance).

A so-called balloon catheter is already in use in conformal radiation therapy of the prostate. Before the computer tomography images that serve to plan the radiation therapy are produced, and before each individual radiation treatment, a catheter that possesses a fillable, expandable catheter head is introduced into the rectum through the anus, and filled with a predetermined amount of water. In the process, the prostate is pressed against the pubic bone by the expanded catheter head, and thereby brought into a more or less reproducible position during the radiation treatments. In spite of this, the wall of the rectum that is adjacent to the prostate receives a dose of radiation that is not without risk, since the position of this part of the intestine is not sufficiently known. The requirement of conformal avoidance is therefore not met.

It is therefore the object of the present invention to provide a device with which conformal avoidance is optimized, i.e., improved.

This object is accomplished with the measures indicated in the characterizing portion of Claim 1. Advantageous modifications of the invention and its use ensue from the further claims.

The invention consists of a special catheter that has at least one expandable part; according to the invention, at least one sensor for determining the position is provided, preferably on the inside surface of one of the expandable parts.

In a preferred embodiment of the device according to the invention, the catheter contains an expandable part that simultaneously forms the catheter head. In the case of radiation therapy of the prostate, the catheter according to the invention, like the balloon catheter known from the prior art, is introduced into the rectum and subsequently filled with water and/or air. The sensor contained in the catheter head is used to measure the position in three coordinates, and the orientation in two angles. The catheter is embodied such that, after the catheter has been positioned and filled, the sensor rests snugly against the inside of the part of the intestinal wall that is immediately adjacent to the prostate and is particularly supposed to be protected against a risky dose of radiation. The sensor position and orientation can be constantly monitored during the radiation process for optimal conformal avoidance of irradiation of the risk region of the rectum wall, since they indicate possible displacements of this region. Either the radiation process is interrupted if the intestinal wall (the risk organ) moves, and is resumed when the wall goes back into position, or the radiation field is continuously adapted to the position of the tumor and the intestinal wall.

The invention is explained in greater detail below with reference to a drawing. The single drawing shows a catheter according to the invention in a schematic, cutout view; this catheter is introduced into a body cavity, with a catheter head being expanded to fix a body part in place.

The single FIGURE shows a device according to the invention for frequently recurring, precise measurement of the position of certain healthy organs or parts thereof, referred to hereinafter as risk organs RO, to prevent damage to the organs during radiation therapy of immediately adjacent tumors. The device according to the invention comprises a catheter K, a catheter head KK produced from an expandable material, and a sensor PS for determining position. At its distal end, the catheter K changes over into a catheter head KK, with the catheter K and the catheter head KK forming an airtight, sealed unit, with the exception of an opening O, at this end of the catheter K.

The single FIGURE shows the device according to the invention being introduced into a cavity through a body orifice KO. The catheter head KK is expanded by the supply of water and/or air, which has or have been conveyed through the opening O. The position sensor PS that is attached to the inside surface of the catheter head KK is pressed against a risk organ RO that is supposed to receive the lowest possible dose of radiation.

The sensor PS generates electrical signals. These are transmitted to the outside, either wireless or via a fine wire connection DV that runs through the inside of the catheter K and the catheter head KK, out of the body, and is fed into a receiver unit (not shown in the FIGURE). There, the position of the sensor PS and its orientation are determined repeatedly at a high frequency, for example 50 times per second, using hardware and software. It has been seen that the device described in WO 97/36 192 is particularly suitable for determining position.

The device according to the invention is particularly suitable for treating the prostate. The device according to the invention can, however, be used successfully whenever natural body orifices (nose, mouth, intestine, vagina) can be used in conformal radiation therapy and conformal radiation avoidance.

In a further embodiment of the invention, a dose rate unit SD is integrated, preferably directly next to the sensor PS for determining the position; this unit can be used to check whether the radiation dose in the risk organ RO is being kept at the desired low level.

A further embodiment of the invention includes a marking MK on a part of the catheter K that is located outside the patient's body during the treatment. The marking MK indicates the position of the sensor PS or the dose rate unit SD relative to the axis of the catheter K. This marking MK serves to introduce the catheter K correctly, not twisted.

In a further embodiment of the invention, additional sensors (not shown in the FIGURE) are provided on the inside and/or outside surface of the catheter head KK. For example, an $O_2$ sensor (oxygen sensor) can provide information that is important to the radiologist.

Although it has been explicitly pointed out that the sensor PS for determining position should be placed as close as possible to a risk organ RO that must not be irradiated, or may only be irradiated as little as possible, it is a simple adaptation of the use of the inventive device, based on the teaching described herein, to position the sensor PS or the dose rate unit SD as close as possible to a body part that is to be irradiated.

The invention claimed is:

1. A device comprising:
 a catheter for introduction into a body having a body part a portion of which is in an immediate vicinity of a tumor to be irradiated, the catheter including:
   at least one expandable portion enabled to expand within an interior of the body to minimize a movement of the body part; and
   at least one sensor unit fixedly disposed within the at least one expandable portion, the at least one sensor unit to provide a position signal indicative of a current position of the at least one sensor unit,
   the at least one expandable portion being positioned within the body so that in an expanded state, the at least one sensor unit is positioned adjacent to the portion of the body part that is in the immediate vicinity of the tumor;
 a receiver unit, positioned outside the body, to receive the position signal provided by the sensor unit and to determine whether the at least one sensor unit has exhibited a movement based on the position signal; and
 a conformal radiation unit, positioned outside the body, to adapt a shape of a radiation field if the receiver unit determines that the at least one sensor unit has exhibited a movement.

2. The device of claim 1 further comprising a signal path for connecting the sensor unit and the receiver unit.

3. The device of claim 2 wherein the signal path is a wire positioned within the catheter.

4. The device of claim 1 wherein the catheter includes a single expandable portion positioned proximate the head of the catheter.

5. The device of claim 1 further comprising a dose rate unit positioned within the expandable portion of the catheter, wherein the dose rate unit provides a signal that is receivable by the receiver unit.

6. The device of claim 5 wherein the dose rate unit is positioned proximate the sensor unit.

7. The device of claim 5 further comprising a signal path for connecting the dose rate unit and the receiver unit.

8. The device of claim 7 wherein the signal path is a wire positioned within the catheter.

9. The device of claim 1 wherein the catheter includes a marking.

10. A method comprising:
 positioning a catheter including a sensor unit within an interior of a body such that the sensor unit is adjacent to a portion of a body part that is in an immediate vicinity of a tumor to be irradiated;
 expanding an expandable portion of the catheter to minimize a movement of the body part in proximity to the expandable portion;
 determining based on a position signal provided by the sensor unit whether the sensor unit has exhibited a movement; and
 adapting a shape of a radiation field generated by a conformal radiation unit positioned outside the body if the receiver unit determines that the at least one sensor unit has exhibited a movement.

11. The method of claim 10 wherein expanding an expandable portion of the catheter includes providing pressurized water to the expandable portion of the catheter.

12. The method of claim 10 wherein expanding an expandable portion of the catheter includes providing pressurized air to the expandable portion of the catheter.

13. The method of claim 10 further comprising monitoring the radiation dose provided by the radiation unit using a dose rate unit positioned proximate the sensor unit.

14. The device of claim 1 wherein the at least one sensor unit is fixedly disposed on an inside surface of the at least one expandable portion.

15. The device of claim 1 wherein the position signal comprises:
 three coordinates; and
 two angles.

16. The method of claim 10 wherein the position signal comprises:
 three coordinates; and
 two angles.

17. The device of claim 1 wherein at least one of the sensor units comprises a oxygen sensor.

* * * * *